(12) United States Patent
Palushi et al.

(10) Patent No.: US 11,998,284 B2
(45) Date of Patent: Jun. 4, 2024

(54) ARTICULATING GUIDE WITH INTEGRAL POSITION SENSOR

(71) Applicant: Acclarent, Inc., Irvine, CA (US)

(72) Inventors: Jetmir Palushi, Irvine, CA (US); Jonathan A. Syby, Manasquan, NJ (US); Itzhak Fang, Irvine, CA (US); Michelle Higley, Irvine, CA (US)

(73) Assignee: Acclarent, Inc., Princeton, NJ (US)

( * ) Notice: Subject to any disclaimer, the term of this patent is extended or adjusted under 35 U.S.C. 154(b) by 637 days.

(21) Appl. No.: 16/670,190

(22) Filed: Oct. 31, 2019

(65) Prior Publication Data

US 2020/0179059 A1 Jun. 11, 2020

Related U.S. Application Data

(60) Provisional application No. 62/776,680, filed on Dec. 7, 2018.

(51) Int. Cl.
*A61B 34/20* (2016.01)
*A61B 1/00* (2006.01)
(Continued)

(52) U.S. Cl.
CPC .......... *A61B 34/20* (2016.02); *A61B 1/00154* (2013.01); *A61B 1/015* (2013.01);
(Continued)

(58) Field of Classification Search
CPC ..... A61B 1/00154; A61B 34/20; A61B 1/015; A61B 1/07; A61B 5/062; A61B 17/00234;
(Continued)

(56) References Cited

U.S. PATENT DOCUMENTS 7,720,521 B2 5/2010 Chang et al.
2006/0184016 A1* 8/2006 Glossop ............... A61B 1/2676
600/434
(Continued)

FOREIGN PATENT DOCUMENTS

WO WO-2013056006 A2 * 4/2013 ......... A61B 1/00006
WO WO-2015088961 A1 * 6/2015 ......... A61B 10/0283
WO WO-2018045465 A1 * 3/2018 ............. A61B 34/20

OTHER PUBLICATIONS

U.S. Appl. No. 62/741,594, entitled "Hollow Tube Surgical Instrument with Single Axis Sensor," filed Oct. 5, 2018.

*Primary Examiner* — John D Li
(74) *Attorney, Agent, or Firm* — Eva Tan (57) ABSTRACT

A guide sheath includes ports at a handle portion through which flexible endoscopic tools may be advanced until they emerge from corresponding ports at a distal tip of the guide sheath. The guide sheath includes a position sensor at its distal tip that is compatible with an image guided surgery (IGS) system, such that a virtual view of the distal tip's position relative to a surgical site may be presented by the IGS system. The virtual view may assist a surgeon in precisely positioning the distal tip at the surgical site, and then one or more flexible endoscopic tools may be advanced the length of the guide sheath for use at the surgical site. The guide sheath may also include an articulating portion at the distal tip that may be deflected in one or more directions in order to provide additional control over placement within the surgical site.

20 Claims, 7 Drawing Sheets

(51) Int. Cl.
*A61B 1/015* (2006.01)
*A61B 1/07* (2006.01)
*A61B 5/06* (2006.01)
*A61B 17/00* (2006.01)
*A61B 17/24* (2006.01)
*A61M 25/01* (2006.01)
*A61M 25/09* (2006.01)

(52) U.S. Cl.
CPC ............... *A61B 1/07* (2013.01); *A61B 5/062* (2013.01); *A61B 17/00234* (2013.01); *A61B 2017/0034* (2013.01); *A61B 17/24* (2013.01); *A61B 2034/2051* (2016.02); *A61M 25/0127* (2013.01); *A61M 25/09* (2013.01)

(58) Field of Classification Search
CPC ............ A61B 17/24; A61B 2034/2051; A61B 2017/0034; A61M 25/0127; A61M 25/09
USPC .......................................................... 600/424
See application file for complete search history.

(56) References Cited

U.S. PATENT DOCUMENTS

| | | | |
|---|---|---|---|
| 2009/0292171 A1* | 11/2009 | Ito | A61B 5/064 600/111 |
| 2010/0234724 A1* | 9/2010 | Jacobsen | A61B 34/20 600/424 |
| 2013/0204124 A1* | 8/2013 | Duindam | A61B 5/062 604/272 |
| 2014/0364725 A1 | 12/2014 | Makower | |
| 2015/0327757 A1* | 11/2015 | Rozenfeld | A61B 1/267 600/190 |
| 2016/0008083 A1 | 1/2016 | Kesten et al. | |
| 2016/0045097 A1* | 2/2016 | Smith | A61M 25/0147 604/95.04 |
| 2017/0209672 A1* | 7/2017 | Hart | A61B 90/03 |
| 2017/0340350 A1* | 11/2017 | Lieberman | A61B 1/0008 |
| 2018/0099125 A1* | 4/2018 | Richer | A61M 25/09041 |
| 2018/0110403 A1* | 4/2018 | Okazaki | A61B 1/0661 |
| 2018/0310886 A1 | 11/2018 | Salazar et al. | |
| 2018/0311472 A1 | 11/2018 | Matlock et al. | |
| 2019/0015645 A1 | 1/2019 | Matlock et al. | |

* cited by examiner

ARTICULATING GUIDE WITH INTEGRAL POSITION SENSOR

PRIORITY

This application claims priority to U.S. Provisional Patent 62/776,680, filed Dec. 7, 2018 and entitled Articulating Guide with Integral Position Sensor.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

IGS technology may be utilized to aid in the precise positioning of surgical instruments relative to anatomical regions associated with a surgical procedure. However, not all surgical instruments are compatible with IGS techniques, since detecting and determining the position of the surgical instrument may require that the instrument include sensors or other devices that enable it to communicate with the IGS navigation (e.g., by detecting a magnetic field, affecting a magnetic field, or performing wireless triangulation techniques). As a result, many standard tools that a surgeon may wish to use during a surgical procedure may be undetectable and non-navigable by the IGS navigation system. For example, varying types of endoscopic tools such as scissors, biopsy needs and collectors, debriders, laser cutters and cauterizers, and other similar tools may not contain sensors or other devices that allow them to be tracked and displayed to a surgeon during use. Even where tools are available in implementations that are trackable by an IGS navigation system, the integration of sensors or other devices to make such tracking possible increases the cost and complexity relative to similar tools that are not tracked.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

Figure 1:
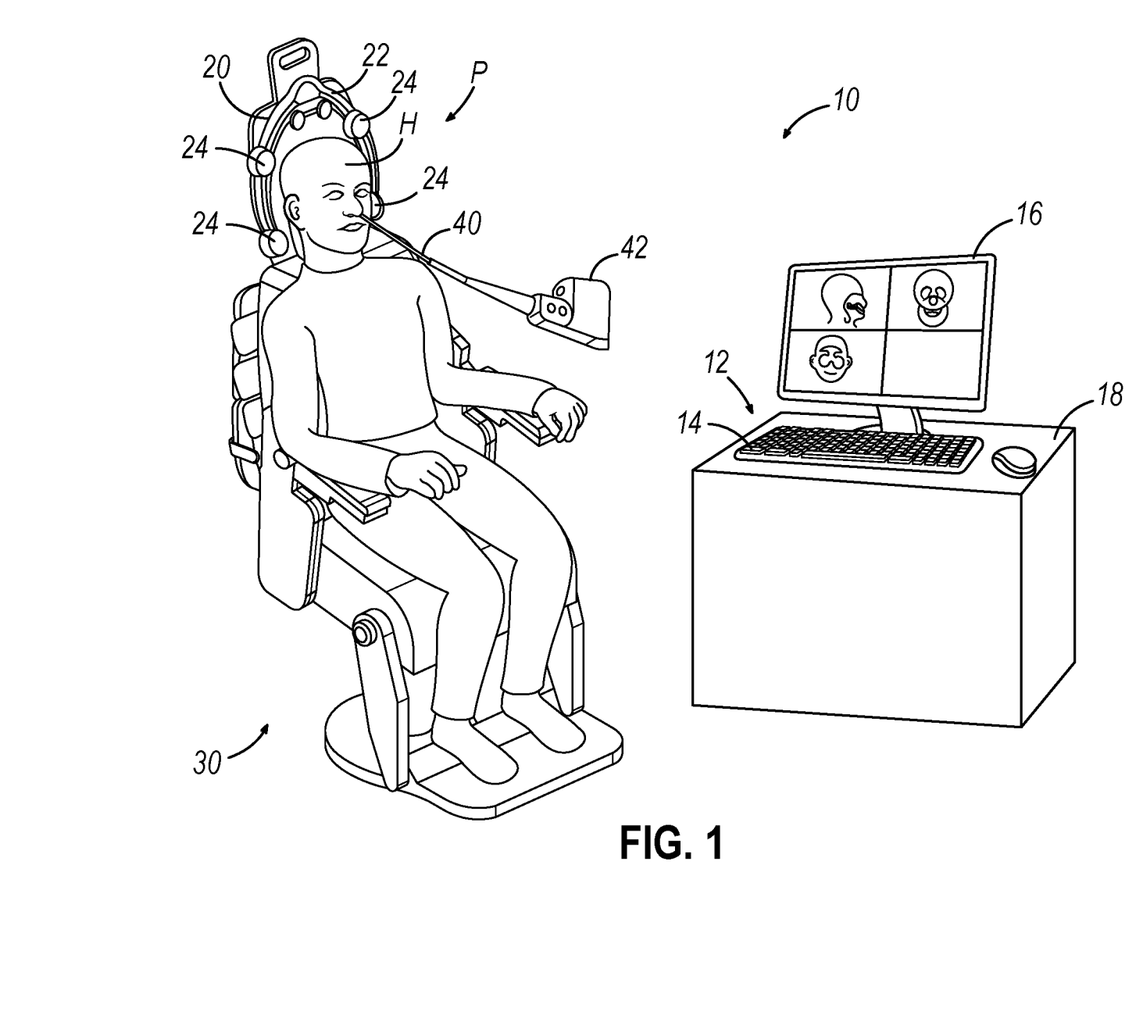
FIG. 1 depicts a schematic view of an exemplary surgery navigation system being used on a patient seated in an exemplary medical procedure chair.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pub. No. 2018/0310886, entitled "Apparatus to Secure Field Generating Device to Chair," published Nov. 1, 2018, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24). A coupling unit (42) is secured to the proximal end of navigation guidewire (40) and is configured to provide communication of data and other signals between console (18) and navigation guidewire (40). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40) or other medical instrument (e.g., dilation instrument, surgical cutting instrument, etc.) within a three-dimensional space (i.e., within the head (H) of the patient (P), etc.). To accomplish this, processor (12) executes an algorithm to calculate location coordinates of the distal end of navigation guidewire (40) from the position related signals of the coil(s) in navigation guidewire (40). While the position sensor is located in guidewire (40) in this example, such a position sensor may be integrated into various other kinds of instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, the disclosure of which is incorporated by reference herein. In the event that the operator is also using an endoscope, the endoscopic image may also be provided on display screen (16).

The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. Exemplary Guide Sheath

Figure 2:
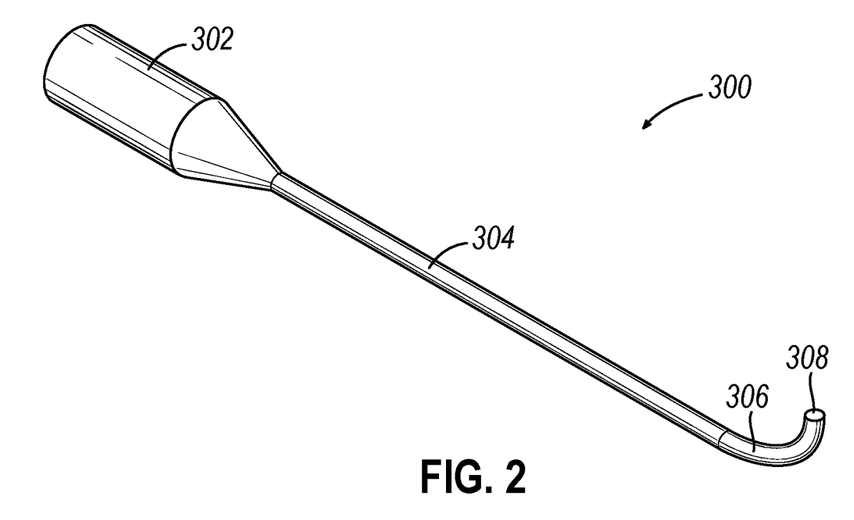
FIG. 2 depicts a perspective view of an exemplary guide sheath usable with the surgery navigation system of FIG. 1.
Figure 3:
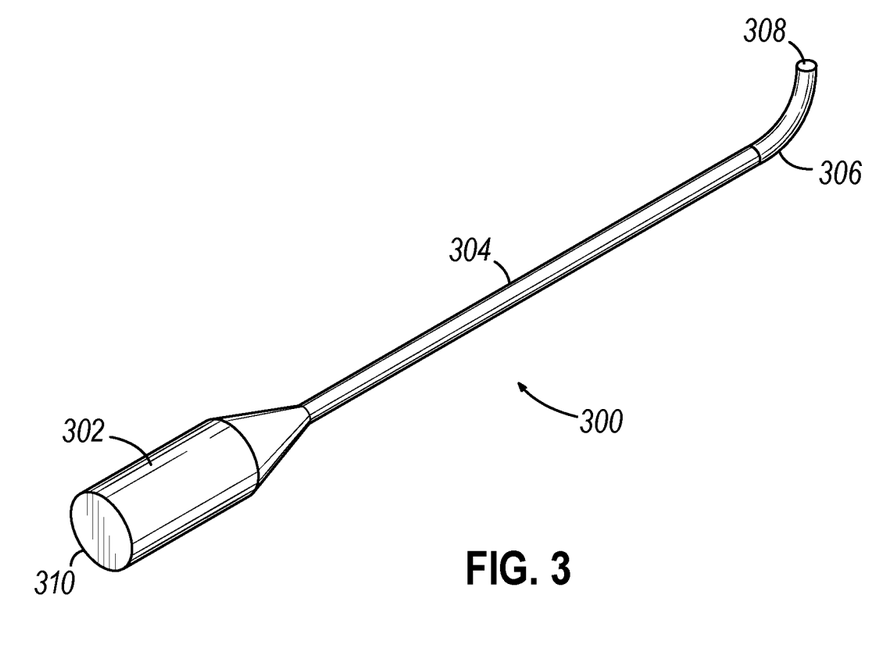
FIG. 3 depicts another perspective view of the guide sheath of FIG. 2.

As some surgical tools and instruments may not include an integral position sensor, it may be advantageous to provide a variable use guide sheath that is trackable by the IGS navigation system (10). For example, FIGS. 2 and 3 show a guide sheath (300) that may receive one or more flexible tools or instruments that may not otherwise be trackable by the IGS navigation system (10), and aid in positioning such tools at a surgical site. The guide sheath (300) includes a handle (302) from which a shaft (304) extends. The shaft (304) may be of a length and diameter suitable for placement within various passageways in the ear, nose, and throat, and may vary in size depending upon a particular application (e.g., for use in children or adults of various sizes).

An articulating portion (306) is positioned at a distal end of the shaft (304), and a destination port (308) is positioned at a distal end of the articulating portion (306). The articulating portion (306) may be remotely flexed laterally in one or more directions relative to the shaft (304), in order to aid in navigating the guide sheath (300) through anatomical passageways in the ear, nose, or throat of a patient, thereby facilitating positioning of the destination port (308) precisely at a surgical site, as will be described in more detail below in the context of FIGS. 8A and 8B. As can be seen in FIG. 3, the proximal end of the handle (302) includes an origin port (310). The origin port (310) includes openings to one or more enclosed channels that pass though the handle (302), along the shaft (304), and terminate at corresponding openings in the destination port (308), as will be described in more detail below.

Figure 4:
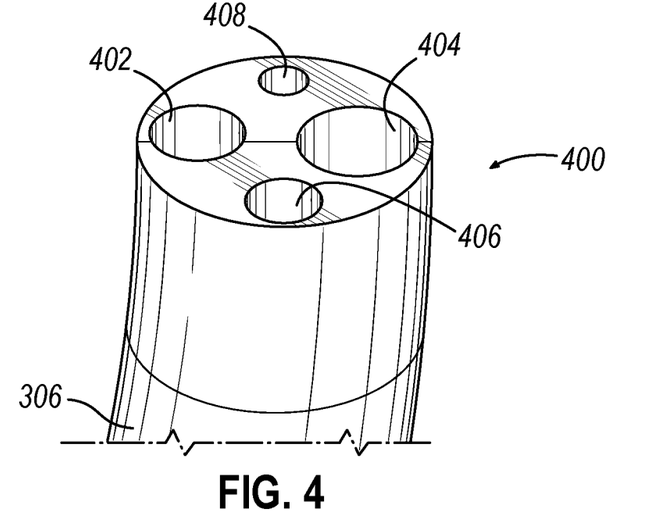
FIG. 4 depicts an enlarged perspective view of a distal end of the guide sheath of FIG. 2.
Figure 5:
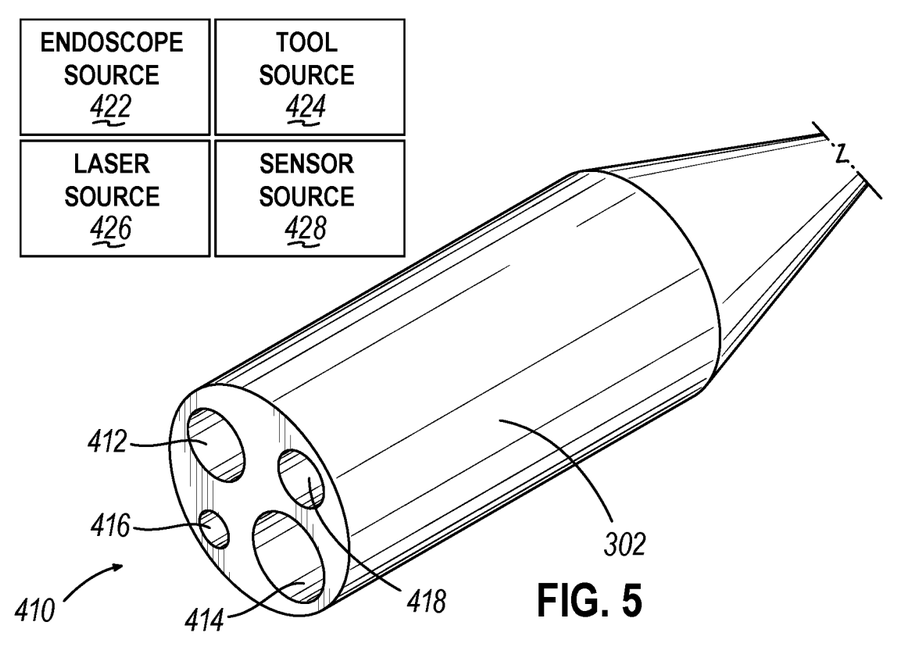
FIG. 5 depicts an enlarged perspective view of a proximal end of the guide sheath of FIG. 2.

For example, FIGS. 4 and 5 respectively depict a front perspective view of an exemplary destination port (400) and a corresponding exemplary origin port (410) that may be implemented in a guide sheath or other guide device such as the guide sheath (300). The destination port (400) includes an endoscope channel opening (402) that corresponds to an endoscope channel opening (412) in the origin port (410), such that an endoscope channel (not shown) extends along the length of guide sheath (300) from opening (402) to opening (412). A flexible tool, such as an endoscope, may be inserted into the endoscope channel opening (412) and advanced along the endoscope channel through the shaft (304) until the distal end of the endoscope emerges from the endoscope channel opening (402).

The destination port (400) also includes a tool channel opening (404), which corresponds to a tool channel opening (414) in the origin port (410), such that a tool channel (not shown) extends along the length of guide sheath (300) from opening (404) to opening (414). A flexible tool such as a tissue cutting device may be inserted into the tool channel opening (404) and advanced through the channel to emerge at the tool channel opening (404) of the destination port (400). The tool channel opening (414) and endoscope channel opening (402) may be sized to receive a variety of flexible tools, such that multiple endoscopes may be deployed (e.g., one in the endoscope channel and one in the tool channel), multiple tissue affecting tools may be deployed (e.g., a scissor in the tool channel and a cauterizing tool in the endoscope channel), or other configurations and arrangements as may be desired.

The destination port (400) also includes a laser channel opening (406) which corresponds to a laser channel opening (416) in the origin port (410), and a sensor channel opening (408) that corresponds to a sensor channel opening (418) in the origin port (410). A laser channel (not shown) extends along the length of guide sheath (300) from opening (406) to opening (416); and a sensor channel (not shown) extends along the length of guide sheath (300) from opening (408) to opening (418). As with other channels, the laser channel may be sized to receive a lighting tool, laser cutting tool, laser cauterizing tool, or other tool to produce varying combinations of tools usable at the surgical site as may be desired. In some variations, laser channel openings (406, 416) and a corresponding laser channel are omitted from guide sheath (300). In some versions where laser channel openings (406, 416) and a corresponding laser channel are omitted from guide sheath (300), destination port (400) or some (other region at the distal end of guide sheath (300)) may include an integral light source (e.g., LED, etc.) that is configured to illuminate a field that is distal to destination port (400).

The sensor channel may be of a size to receive a flexible device that has an integral position sensor, such as the navigation guidewire (40) described above. The sensor-equipped device may be advanced to the distal end of the channel at the destination port (400), such that the position sensor may be located at the distal end of guide sheath (300), thereby enabling IGS navigation system (10) to track the position of the destination port (400) and any tools deployed from destination port (400). In some variations, sensor channel openings (408, 418) and a corresponding sensor channel are omitted from guide sheath (300). In some versions where sensor channel openings (408, 418) and a corresponding sensor channel are omitted from guide sheath (300), destination port (400) or some (other region at the distal end of guide sheath (300)) may include an integral position sensor that is configured to generate position-indicative signals in response to a magnetic field, like the position sensor of navigation guidewire (40) described above.

While tools or instruments may be deployed (e.g., advanced and retracted) through the channels of guide sheath (300), one or more of the channels may also have a tool or instrument permanently or semi-permanently integrated (e.g., fixed with the channel such that it cannot be removed, advanced, or retracted during normal use). For example, where the laser channel is used to provide illumination, an optical light fiber may be integrated therein, since illumination may be provided without advancing the distal end of the fiber outwardly from the end of the laser channel opening (406). Similarly, a position sensor such as a single axis sensor may be integrated within the sensor channel (or elsewhere within the distal end of outer sheath (300)) to provide predictable position tracking at the destination port (400), since it may be tracked without advancing the distal end of the guidewire (40) or other position sensor equipped device outwardly from the end of the sensor channel opening (408). In yet another implementation, each channel may have an integrated tool or instrument. In one example of such an implementation, the tool channel may include an integrated irrigation and suction port operable to deliver irrigation fluid (e.g., saline) to and remove fluids from a surgical site, the laser channel may include a laser fiber through which illumination may be delivered to a surgical site, and the endoscope channel may include an integrated endoscope.

The above-described openings (402, 404, 406, 408, 412, 414, 416, 418) and corresponding channels of guide sheath (300) are just merely illustrative examples. Guide sheath (300) may instead include a greater or lesser number of openings and corresponding channels. Moreover, the above-described openings (402, 404, 406, 408, 412, 414, 416, 418) and corresponding channels of guide sheath (300) may be used for various alternative purposes, beyond the exemplary purposes described above. Other suitable configurations, arrangements, and uses will be apparent to those skilled in the art in view of the teachings herein.

Some tools or instruments that are inserted into guide sheath (300) may also be connected to a power source, light source, vacuum source, or other system before or after the tool or instrument is advanced into the appropriate channel of guide sheath (300). For example, an endoscope source (422) may attach to a proximal end of an endoscope and provide electrical power and data communication (e.g., receiving images via fiber optics, receiving digital images via data connection) with an endoscope that is advanced to the destination port (400) via the endoscope channel of guide sheath (300). A tool source (424) may be connected to a surgical tool (e.g., a cutting or debriding device, etc.) and may provider power and control over the function of the tool when the tool is advanced to the destination port (400) via the tool channel of the guide sheath (300). A laser source (426) may similarly provide illumination or laser power when connected to a laser tool advanced to the destination port (400) via the laser channel of the guide sheath (300). A sensor source (428) may be connected to a position sensor such as the navigation guidewire (40), and may provide power, or receive data (e.g., as a result of interactions with the magnetic field) that may be provided to the IGS navigation system (10) to be used for positional tracking. By way of example only, sensor source (428) may be analogous to coupling unit (42) referred to above.

An implementation of the guide sheath (300) having the destination port (400) and the origin port (410) may be advantageous in that it provides multiple, variable use channels that may be positioned, by the guide sheath (300), at various locations within the ear, nose, or throat of a patient. In this manner, varying combinations and configurations of tools may be deployed through the guide sheath (300) with the benefit of position tracking provided by a position sensor such as the navigation guidewire (40) integrated in the sensor channel opening (408). Moreover, guide sheath (300) may provide structural guidance to inserted tools and instruments to reach anatomical regions that such tools or instruments might otherwise have great difficulty reaching (e.g., guiding an inserted tool or instrument to reach around a turbinate, uncinate process, or other anatomical structure within a nasal cavity). Other variations exist and may be advantageously implemented with the guide sheath (300).

Figure 6:
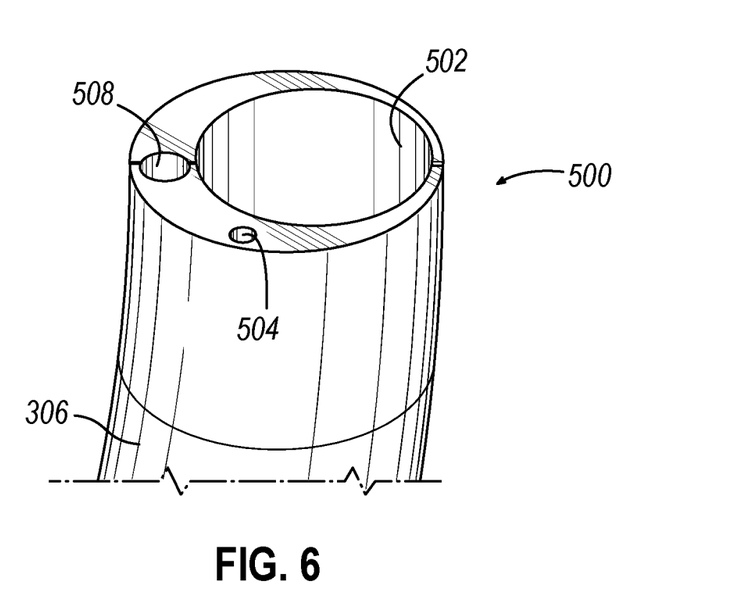
FIG. 6 depicts an enlarged perspective view of an alternate distal end of the guide sheath of FIG. 2.
Figure 7:
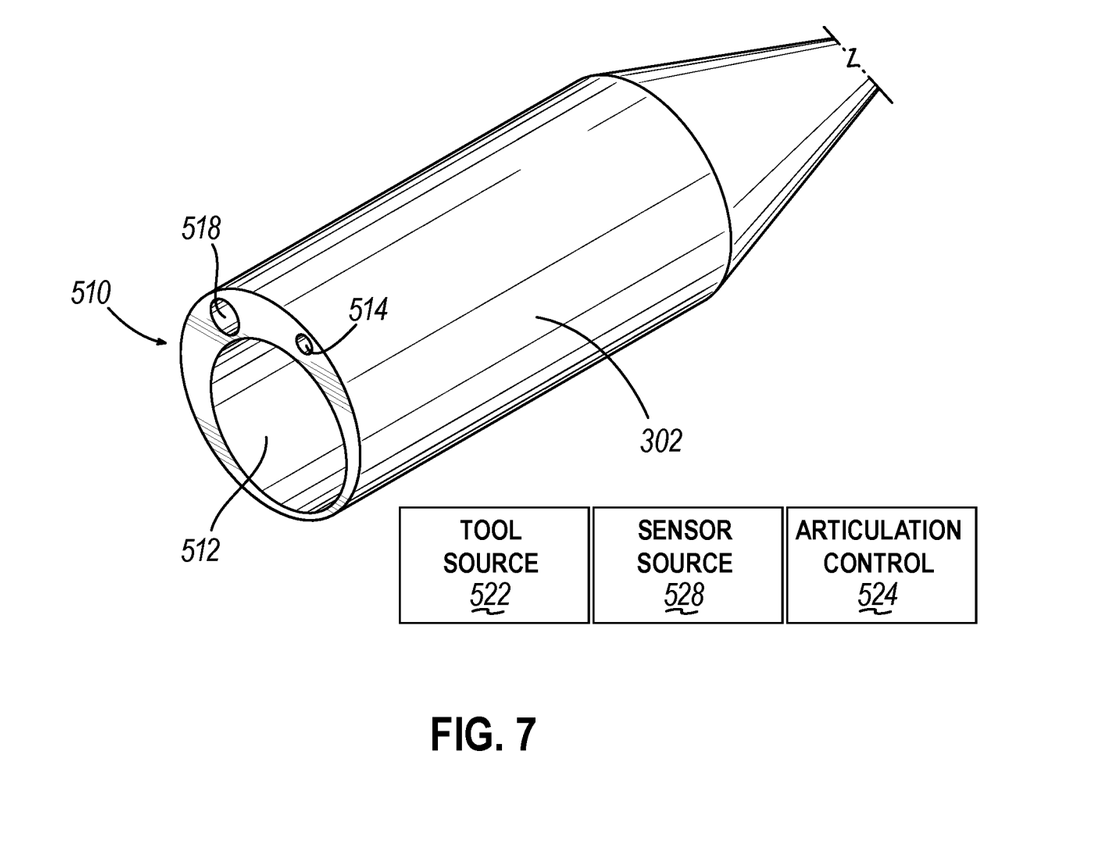
FIG. 7 depicts an enlarged perspective view of an alternate proximal end of the guide sheath of FIG. 2.

For example, FIGS. 6 and 7 depict a front perspective view of an exemplary alternative destination port (500) and an exemplary alternative origin port (510) that may be incorporated into a guide sheath such as the guide sheath (300). The destination port (500) of this example includes a tool channel opening (502) that corresponds to a tool channel (512) of the origin port (510). A flexible tool (e.g., cutting instrument, shaver, curette, suction instrument, etc.) may be passed into tool channel opening (512), advanced through the shaft (304), and extended distally from the tool channel opening (502).

Destination port (500) of the present example also includes a control wire opening (504), with origin port (510) of the present example including a corresponding control wire opening (514), which may house a control wire (not shown). The control wire may be movable within the control wire channel and fixed at a point proximate to the destination port (500) (e.g., fixed at the control wire opening (504) or fixed within the articulating portion (306)). The control wire may be translated longitudinally within the control wire channel in order to cause the articulating portion (306) to flex in a corresponding lateral direction.

The example shown in FIGS. 6 and 7 also includes a sensor channel opening (508) and a corresponding sensor channel opening (518) that form a sensor channel, similar in function to the sensor channel opening (408) and sensor channel opening (418) described above in the context of FIGS. 4 and 5. As another merely illustrative alternative, destination port (500) may include an integral position sensor. By providing a larger variable use channel such as the tool channel accessible via the tool channel opening (502) and the tool channel opening (512), larger tools may be deployed through the guide sheath (300) having the ports (500, 510) shown in FIGS. 6 and 7; as compared to smaller channels, such as those shown in the embodiment of FIGS. 4 and 5. To the extent that some options in deploying varying combinations and configurations of tools, instruments, or other devices through guide sheath (300) may be lost by enlarging the diameter of openings (502, 512) and the corresponding tool channel, it may be advantageous to provide a reduced number of larger channels that can accommodate even the largest flexible tools being advanced therein. Variations on the number, position, and purpose of channels exist beyond those shown in FIGS. 4-7, and such variations will be apparent to one of ordinary skill in the art in light of this disclosure.

FIG. 7 also shows a tool source (522) that may be connected to a tool deployed within the tool channel to provide power and control, and a sensor source (528) (e.g., coupling unit (42)) that may be connected to a sensor device deployed within or integrated within the sensor channel to provide power, data communication, or other functionality. An articulation control (524) may be attached to a proximate end of a control wire extending from the control wire opening (514), and may be operated to retract the control wire, thereby causing the articulating portion (306) to deflect or flex laterally to the desired degree and position. When the articulation control (524) thereafter extends or releases the tension on the control wire, the articulating section (306) may be flexibly biased such that it returns to its original, unflexed position. Various suitable components and configurations that may be incorporated into articulation control (524) to drive translation of the control wire will be apparent to those skilled in the art in view of the teachings herein.

Figure 8A:
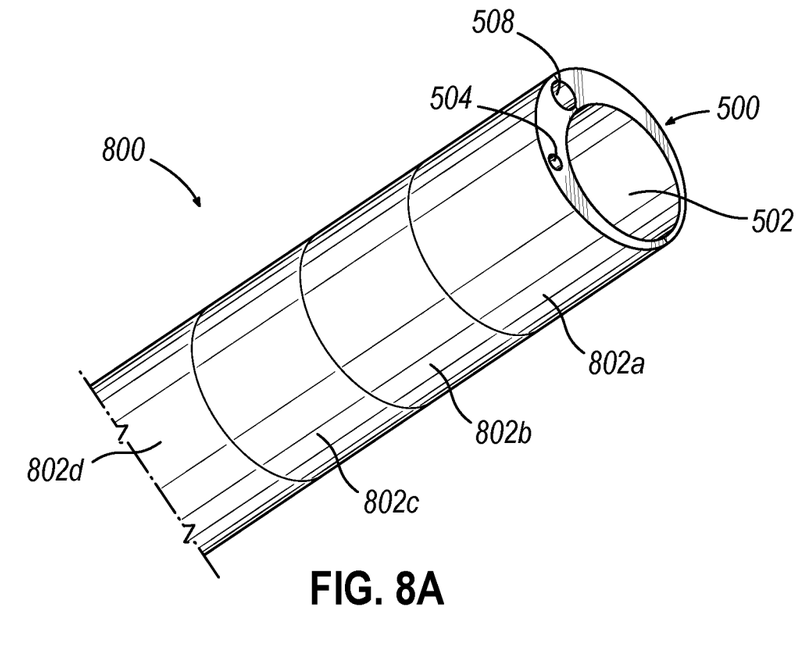
FIG. 8A depicts an enlarged perspective view of an exemplary articulating portion of the guide sheath of FIG. 2 in a straight configuration.
Figure 8B:
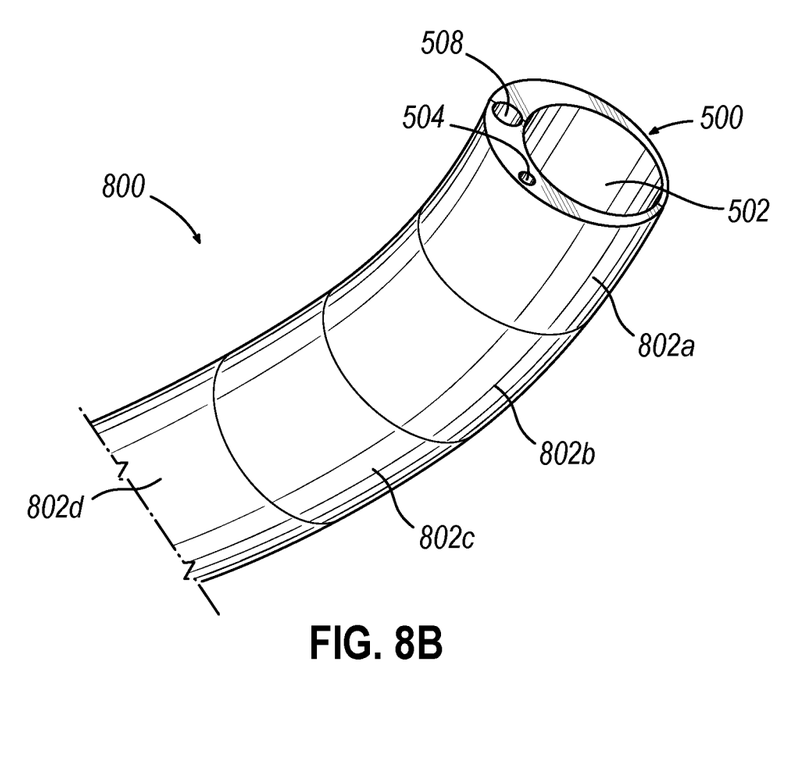
FIG. 8B depicts an enlarged perspective view of the articulating portion of the guide sheath of FIG. 2 in an articulated configuration.

For example, FIG. 8A depicts a front perspective view of an exemplary articulating portion (800) in a straight configuration, while FIG. 8B depicts a front perspective view of the articulating portion (800) in an articulated configuration. The articulating portion (800) includes a first section (802a), a second section (802b), a third section (802c), and a fourth section (802d), arranged as adjacent segments that are movable relative to each other. While four sections are shown in this example, other implementations of an articulating portion may have varying numbers or types of sections, other flexible or movable portions, or other components and configurations. In some versions of the present example, each section may be movably attached to the subsequent section, with the first section (802a) including the destination port (500). As the control wire is retracted (e.g., either manually, or by use of the articulation control (524)), the sections may shift to accommodate the shortening length of the control wire, causing the articulating portion (800) to flex, in response, from a straight configuration to a curved or articulated position such as that shown in FIG. 8B. When tension on the control wire is released, connections between each section may be flexibly biased towards a neutral position such as that shown in FIG. 8A, so that the articulating portion (800) gradually returns to the neutral position or straight configuration as tension is eased.

The articulating portion (800) is an exemplary implementation of the articulating section (306), and it should be understood that variations exist. By way of further example only, articulating section (306) may be constructed and operable in accordance with at least some of the teachings of U.S. Pub. No. 2018/0311472, entitled "Deflectable Guide for Medical Instrument," published Nov. 1, 2018; and/or U.S. patent application Ser. No. 16/032,471, entitled "Adjustable Instrument for Dilation of Anatomical Passageway," filed Jul. 11, 2018, the disclosure of each of which is incorporated by reference herein.

It should also be understood that variations on the type, placement, and configurations of position sensors such as might be installed or integrated within sensor channel opening (408) and the sensor channel opening (508) exist. By way of further example only, such position sensors may be constructed and operable in accordance with at least some of the teachings of U.S. Pat. App. No. 62/741,594, entitled "Hollow Tube Surgical Instrument with Single Axis Sensor", filed Oct. 5, 2018, the disclosure of which is incorporated by reference herein.

Figure 9A:
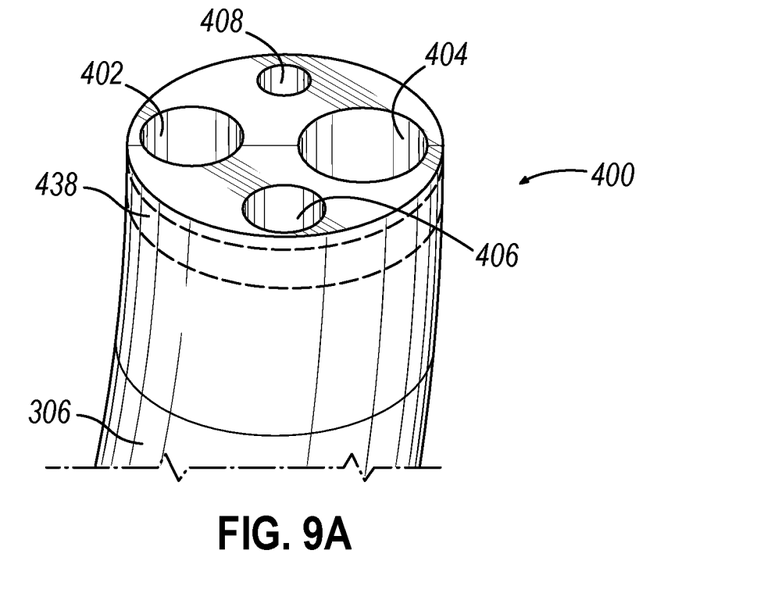
FIG. 9A depicts an enlarged perspective view of the distal end of FIG. 4 with the position of an exemplary circumferential sensor indicated by a set of dashed lines.
Figure 9B:
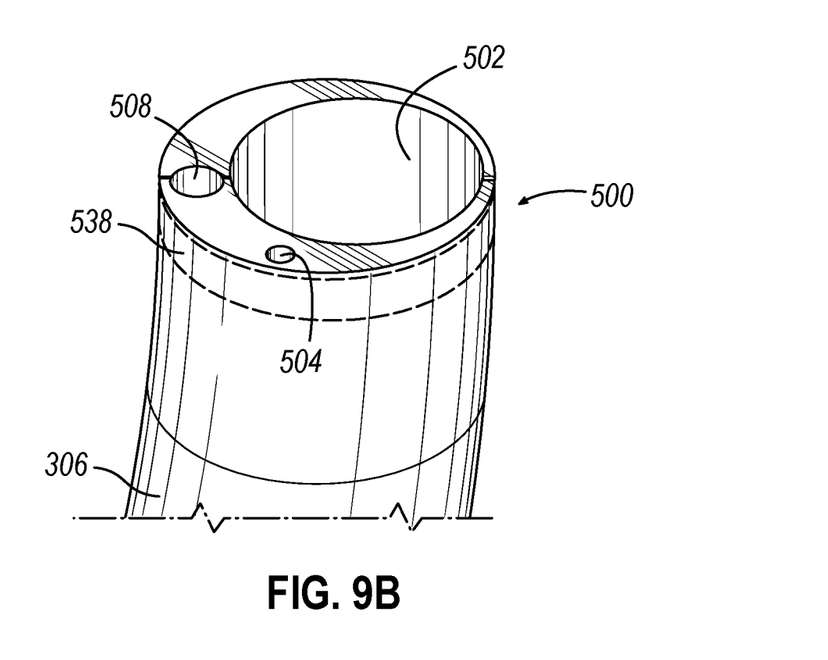
FIG. 9B depicts an enlarged perspective view of the distal end of FIG. 6 with the position of an exemplary circumferential sensor indicated by a set of dashed lines.

For example, FIGS. 9A and 9B show enlarged perspective views of the distal end of FIGS. 4 and 6 respectively, with the position of an exemplary circumferential sensor indicated in each by a set of dashed lines. With reference to FIG. 9A, a circumferential sensor (438) may be positioned at the distal tip (400) within a section of the articulating portion (306), or on the exterior surface of a section of the articulating portion (306). The circumferential sensor (438) may include two or more position sensors, functioning similarly to the guidewire (40), that are offset from each other at positions around the circumference of the circumferential sensor (438), and that are independently trackable by the IGS navigation system (10) via one or more wires, cables, or other connections that may be positioned or integrated within the sensor channel. With reference to FIG. 9B, a circumferential sensor (538), having similar features and functions as the circumferential sensor (438), is positioned at the distal tip (500). The circumferential sensor (538) may also include two or more position sensors that are independently trackable by the IGS navigation system (10) via a connection installed or integrated within the sensor channel.

Use of a sensor such as the circumferential sensor (438, 538) with any one or more of the articulating guides described herein may be advantageous in that it can provide a more accurate representation of the articulating guide as compared to a single tracked point. For example, where a single position sensor is positioned at or within the sensor channel opening (408), the position of that point of the articulating guide within three dimensional space may be determined by the IGS navigation system (10), but determining the orientation of the articulating guide within three dimensional space may require additional information or estimation. Where a circumferential sensor such as the circumferential sensor (438) is positioned at the distal tip (400), the position of each of the independently trackable points about the circumference of the circumferential sensor (438) may be determined by the IGS navigation system (10), and used, along with known information such as their static positioning relative to each other, to determine an orientation of the distal tip (400) within three dimensional space. The circumferential sensor (438) may also be trackable to provide a more accurate location and representation of the circumference of the distal tip (400), as compared to the location of a single point positioned at the sensor channel opening (408) or elsewhere within the circumference of the distal tip (400).

While use of a position-tracked guide sheath such as the guide sheath (300) allow for various non-tracked tools to be deployed and used during image guided surgery, it may also be advantageous to configure the IGS navigation system (10) to perform steps to determine the configuration of the guide sheath (300) (e.g., whether the articulated portion (306) is straightened or flexed, and to what extent), as well as determine the configuration of any tools deployed therein, when providing the real-time position of the guide sheath (300) relative to a preoperative image set during IGS navigation.

For example, with tracked surgical instruments that have a static form and location for the position sensor, the position of each portion of the instrument relative to the position sensor can always be determined. For instance, for a version of guide sheath without the articulated portion (306), the position of the destination port (308) does not change relative to the position of the shaft (304) during use. This may allow the position of the tool or instrument disposed in guide sheath (300) to be accurately rendered or otherwise represented based solely upon the determined location of the position sensor and known characteristics of the guide sheath (300) (e.g., overall length and other physical features).

In some versions of guide sheath (300), the signal from the position sensor by itself might not provide enough information to determine the extent to with the articulating portion (306) is flexed, and so it may be difficult to accurately render or graphically represent the shaft (304) on a tomographic image or other preoperatively obtained image via display screen (16) of IGS system (10). Similarly, where a tool such as a flexible scissor or other flexible cutting device is deployed to the destination port (308), the IGS navigation system (10) may have difficulties in accurately rendering or representing the distal end of the cutting tool on the tomographic image, since it may extend a distance past the position sensor (e.g., which may be located in the sensor channel opening (408)). It may therefore be advantageous to provide one or more additional position sensors to provide additional position data that supplements the position data from the position sensor at the distal end of guide sheath (300). Such additional position sensors may enable IGS system (10) to determine the extent to which articulating portion (306) is laterally deflected; and the position of the distal end of a tool or instrument disposed in guide sheath (300) relative to the distal end of guide sheath (300).

Figure 10:
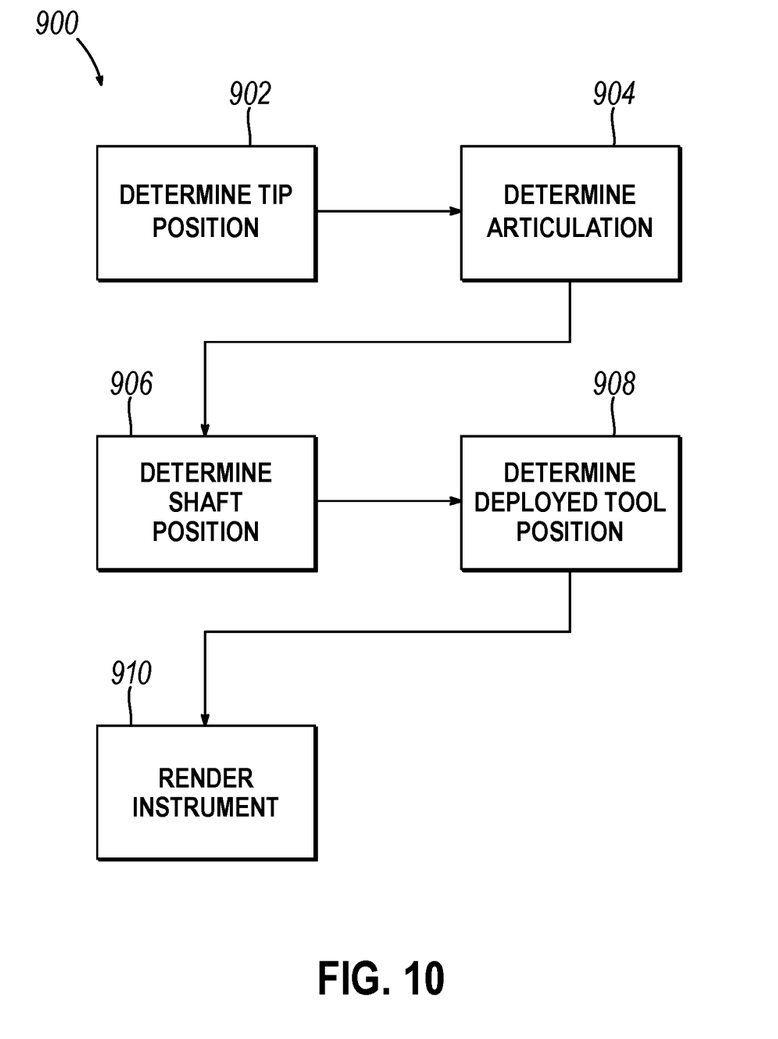
FIG. 10 depicts a flowchart of an exemplary set of steps that may be performed to display the guide sheath of FIG. 2 during an image guided surgery procedure.

As an example, FIG. 10 depicts a flowchart of an exemplary set of steps (900) that may be performed by the IGS navigation system (10) (e.g., by the processor (12) or another device) to display the position of a guide sheath such as the guide sheath (300) during an image guided surgery procedure. When the guide sheath (300) is in use, whether being navigated to a surgical site or already in position at a surgical site for deployment of tools, it may be advantageous to determine characteristics of the guide sheath (300) such as the position of the articulated portion (306) and the position of any deployed tools. To do so, the system may first determine (block 902) a position of the tip of the guide sheath (300) (e.g., the destination port (308)) based upon feedback from a position sensor housed therein (e.g., at the distal end of guide sheath (300)).

The system may then determine (block 904) the current articulation of the articulated portion (e.g., whether, and to what extent, the articulated portion (306) is flexed from a neutral position). This may be accomplished by, for example, placing a second position sensor in the shaft (304) just before the articulation portion (306), and using the tracked distance between the two position sensors to determine the extent of articulation. As another example, the articulation control (524) may be configured or calibrated to determine the currently extended length of the control wire at any time. Such information may be usable by the articulation control (524), processor (12), or another device to determine the extent that the articulated portion (306). In such an example, the articulation control (524) may be configured to determine that 24 inches of control wire must be extended in order for the articulated portion (306) to be straight or unflexed, while retracting the control wire to 20 inches results in the articulated portion (306) being fully flexed. By calibrating each distance in between (e.g., by tenths, hundredths, or other units of inches) and associating it with a corresponding degree of flex (e.g., by degree or distance of displacement), a particular degree of flex may be determined based upon the length of control wire. As yet another example, a compression sensor, object sensor, angular sensor, or other sensor may be integrated in one or more sections of the articulated portion (306); and configured to provide data usable to determine the extent of flex. In this example, a compression sensor, button, or lever may be positioned in the first section (802a) and the such that, as the first section (802a) moves during articulation, it contacts a portion of the second section (802b) and is depressed or receives the force of such contact, with such force or depression corresponding to a predictable level of flex between the two sections.

With the distal tip position determined (block 902), and the level of articulation determined (block 904), the position of the shaft (304) may then be determined (block 906) by the IGS navigation system (10). For example, with reference to FIGS. 8A and 8B, where the shaft (304) attaches to the fourth section (802d), it can be seen that the extent of articulation predictably determines the position of the shaft (304) relative to the location of the position sensor within the sensor channel opening (508). With these three parameters known, as well as other standard specifications for the instrument (e.g., overall length, shaft length, articulating portion length, etc.), the position of the entire guide sheath (300) can then be rendered (block 910) by the IGS navigation system (10) on a tomographic image with an accurate representation of the extent of articulation and position of the shaft (304) relative to the surgical site shown in the tomographic or other preoperative image.

It may be advantageous to also determine (block 908) the position of any tools or instruments that are deployed through the guide sheath (300), especially where such tools are not otherwise tracked directly by the IGS navigation system (10). For example, an endoscope or other device may be able to provide a real-time video image of one or more tools or instruments that are deployed at the surgical site through the guide sheath (300), but if the positions of such tools or instruments are not tracked, it may be difficult to display their position on the tomographic image or other preoperatively obtained image via IGS navigation system (10). Determining (block 908) the position of a deployed tool or instrument may be performed similarly to determining (block 904) the level of articulation.

For example, in the case of a cutting tool or instrument such as a flexible scissor or shaving instrument deployed in the tool channel and extending distally a certain distance beyond the tool channel opening (404) to allow it to interact with tissue, the tool source (424) may be configured to retract and extend the cutting tool or instrument though the guide sheath (300) while determining the length of extension. As with the control wire, an extended length may be calibrated and used to determine a length that the distal, operative portion of the tool or instrument extends from the tool channel opening (404), which may be used by the IGS navigation system (10) to determine (block 908) where the position of the operative portion of the tool or instrument should be displayed on the tomographic image (or other preoperatively obtained image), relative to the destination port (400). In some versions, a graphical representation of the operative portion of the tool is displayed in its real time position on the tomographic image (or other preoperatively obtained image).

As another example, the origin port (410) or the destination port (400) may be configured with a sensor positioned and configured to determine the distance that a tool or instrument has been advanced into the tool channel opening (414). Such a sensor might include, for example, a motion sensor, proximity sensor, or optical sensor configured to detect the movement of the tool or instrument as it advances, while the flexible portion of the tool or instrument itself may be textured, colored, covered with alternating reflective and non-reflective surfaces to aid in being sensed by such an optical sensor. By tracking such distance as the tool or instrument advances relative to the guide sheath (300), the IGS navigation system (10) may determine (block 908) where the position of the operative portion of the tool or instrument should be displayed on the tomographic image; and may include a graphical representation of the extended tool or instrument when rendering (block 910) the position of the operative portion of the tool or instrument.

It should be understood from the foregoing that guide sheath (300) may facilitate access to various anatomical features within the ear, nose, or throat of a patient either with conventional tools or instruments that would be completely incapable of accessing without guide sheath (300) or with conventional tools or instruments that would have great difficulty accessing without guide sheath (300). Unlike a conventional endoscope that includes one or more working channels and articulation capabilities, guide sheath (300) of the present example does not necessarily need to include an integral camera or other imaging feature. Of course, some versions of guide sheath (300) may in fact include an integral camera or imaging feature; or may removably receive a conventional endoscope via a channel extending along the length of guide sheath (300). Also unlike many conventional endoscopes that include one or more working channels and articulation capabilities, guide sheath (300) of the present example is small enough to fit through a patient's nostril and access various regions within the nasal cavity, nasopharynx, etc. Also unlike many conventional endoscopes that include one or more working channels and articulation capabilities, guide sheath (300) of the present example may include an integral position sensor that provides position-indicative signals to IGS navigation system (10).

Those of ordinary skill in the art will also recognize that conventional endoscopes that include one or more working channels and articulation capabilities (e.g., gastroscopes) are simply too long to be practicably used in a patient's head while being disposed through the patient's mouth or nostril. Thus, guide sheath (300) of the present example will have sufficient length to reach any potentially targeted anatomical structures within a patient's head via the patient's nostril or mouth, with the proximal end (e.g., origin port (410, 510)) of guide sheath (300) being positioned just outside of the patient's nostril or mouth. By way of example only, guide sheath (300) may have a length from approximately 4 inches to approximately 7 inches.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A guide sheath comprising: an origin port comprising one or more proximal channel openings; a destination port comprising one or more distal channel openings, wherein the destination port is distal to the origin port; a shaft between the origin port and the destination port, the shaft comprising: one or more channels, wherein each channel of the one or more channels connects one proximal channel opening of the one or more proximal channel openings to one distal channel opening of the one or more distal channel openings, and an articulating portion at a distal end of the shaft, wherein a distal end of the articulating portion is connected to the destination port; and a position sensor located at the destination port, wherein the position sensor is configured to cooperate with an image guided surgery (IGS) navigation system to determine a current position of the position sensor; wherein each channel of the one or more channels is adapted to receive a flexible surgical tool at that channel's proximal channel opening and guide the flexible surgical tool to that channel's distal channel opening as the flexible surgical tool is advanced into that channel.

Example 2

The guide sheath of Example 1, wherein the position sensor is configured to generate an electrical signal in response to a magnetic field, wherein the electrical signal generated by the position sensor is configured to indicate the position of the position sensor within the magnetic field.

Example 3

The guide sheath of any one or more of Examples 1 through 2, wherein the origin port comprises a handle from which the shaft extends, wherein the handle is adapted to be held in a hand during use.

Example 4

The guide sheath of any one or more of Examples 1 through 3, further comprising a navigation guidewire positioned within a channel of the one or more channels, with a distal tip of the navigation guidewire positioned at the destination port, wherein the position sensor is positioned at the distal tip of the navigation guidewire.

Example 5

The guide sheath of any one or more of Examples 1 through 4, wherein the one or more channels comprise a tool channel sized and configured to receive a tool, an endoscope channel sized and configured to receive an endoscope, and an illumination channel sized and configured to receive an illumination source.

Example 6

The guide sheath of Example 5, further comprising: an integrated endoscope positioned within the endoscope channel; an integrated irrigation and suction tool positioned within the tool channel; and an illumination source positioned within the illumination channel.

Example 7

The guide sheath of any one or more of Examples 1 through 6, further comprising a second position sensor located proximal to the articulating portion, wherein the second position sensor is configured to operate with the IGS navigation system to determine a current position of the second position sensor.

Example 8

The guide sheath of any one or more of Examples 1 through 7, further comprising a control wire with a first end fixed at the distal end of the guide sheath and a second end proximal to the first end, such that the second end may be retracted to cause the articulating portion to flex in a first direction.

Example 9

The guide sheath of Example 8, wherein a distance of displacement of the control wire within the guide sheath determines the degree to which the articulating portion flexes in the first direction.

Example 10

The guide sheath of any one or more of Examples 1 through 9, further comprising the IGS navigation system, wherein the IGS navigation system is configured to display the current position of the destination port on a pre-operative image of the surgical site based on a signal from the position sensor.

Example 11

The guide sheath of Example 10, wherein the IGS navigation system is further configured to determine a current flex of the articulating portion and display the articulating portion on the pre-operative image based on the current position and the current flex.

Example 12

The guide sheath of Example 11, wherein the IGS navigation system is further configured to determine a position of a distal end of a deployed tool within a channel of the one or more channels and display the position of the distal end of the deployed tool on the pre-operative image.

Example 13

A method comprising: flexing a distal portion of a shaft of guide sheath to orient a distal end of the shaft at a deflection angle associated with a targeted anatomical structure within a head of a patient; navigating the distal portion of the shaft of the guide sheath to a surgical site within a patient's head, wherein the targeted anatomical structure is at the surgical site; operating an image guided surgery (IGS) navigation system to track a position sensor, wherein the position sensor is located at the distal end of the shaft of the guide sheath; and operating one or more flexible surgical tools at the surgical site, wherein each of the one or more flexible surgical tool is positioned within a channel of the guide sheath, and wherein the channel comprises a proximal channel opening at an origin port of the guide sheath and a distal channel opening at the destination port.

Example 14

The method of Example 13, further comprising inserting the distal portion of the shaft into a nostril of the patient, wherein the act of flexing is performed after the act of inserting.

Example 15

The method of any one or more of Examples 13 through 14, further comprising advancing a flexible surgical tool of the one or more flexible surgical tools into the proximal channel opening of the channel until a distal end of the flexible surgical tool arrives at the distal channel opening of the channel.

Example 16

The method of Example 15, wherein the guide sheath further includes a second channel, the method further comprising advancing a second flexible surgical tool of the one or more flexible surgical tools into a proximal channel opening of the second channel until a distal end of the second flexible surgical tool arrives at a distal channel opening of the second channel.

Example 17

The method of any one or more of Examples 13 through 16, further comprising illuminating the surgical site with an illumination source positioned at the distal end of the shaft.

Example 18

The method of any one or more of Examples 13 through 17, further comprising viewing the surgical site with an imaging device positioned at the distal end of the shaft.

Example 19

An image guided surgery (IGS) navigation system comprising: a magnetic field generator operable to provide a magnetic field; a guide sheath comprising: a shaft defining at least one working channel configured to slidably receive an instrument, wherein the working channel is open at a distal end of the shaft, an articulating portion at the distal end of a shaft, the articulating portion having a distal end, and a position sensor located at or distal to the distal end of the articulating portion, wherein the articulating portion is operable to change the position of the distal end of the articulating portion relative to the shaft; a display; and a processor configured to: determine a current position of the position sensor within the magnetic field, and display a first representation of the position of a distal end of the guide sheath on a preoperative image in real-time based on a signal generated by the position sensor in response to the magnetic field.

Example 20

The IGS navigation system of Example 19, further comprising a flexible tool positioned within the working channel of the guide sheath with a distal end of the flexible tool extending from the distal end of the articulating portion, wherein the processor is further configured to: determine a position of a distal end of the flexible tool, and display a second representation of the position of the distal end of the flexible tool on the preoperative image in real-time.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A guide sheath comprising:
   (a) an origin port comprising a plurality of proximal channel openings;
   (b) a destination port comprising a plurality of distal channel openings, the destination port being distal to the origin port;
   (c) a shaft between the origin port and the destination port, the shaft comprising:
      (i) a plurality of channels, each channel of the plurality of channels connecting one proximal channel opening of the plurality of proximal channel openings to one distal channel opening of the plurality of distal channel openings, the plurality of channels comprising:
         (A) a tool channel, the tool channel being sized and configured to receive a tool,
         (B) an endoscope channel, the endoscope channel being sized and configured to receive an endoscope,
         (C) an illumination channel, the illumination channel being sized and configured to receive an illumination source, and
         (D) a tool tracking sensor, the tool tracking sensor being configured to generate a signal indicating a distance to which a tool is advanced in the tool channel, and
      (ii) an articulating portion at a distal end of the shaft, the articulating portion being configured to articulate, the destination port being distal to the articulating portion, and
      (iii) a straight portion at a proximal end of the shaft, the straight portion being configured to remain straight during articulation of the articulating portion, the origin port being proximal to the straight portion;
   (d) a first position sensor located at the destination port, the first position sensor being configured to cooperate with an image guided surgery (IGS) navigation system to determine a current position of the first position sensor;
   (e) a second position sensor located proximal to the articulating portion and at the straight portion, the second position sensor being configured to operate with the IGS navigation system to determine a current position of the second position sensor;
   (f) an integrated endoscope positioned within the endoscope channel, the endoscope channel being adapted to receive the integrated endoscope at the proximal channel opening of the endoscope channel and guide the integrated endoscope to the distal channel opening of the endoscope channel as the integrated endoscope is advanced into the endoscope channel;
   (g) an integrated irrigation and suction tool positioned within the tool channel, the tool channel being adapted to receive the integrated irrigation and suction tool at the proximal channel opening of the tool channel and guide the integrated irrigation and suction tool to the distal channel opening of the tool channel as the integrated irrigation and suction tool is advanced into the tool channel; and
   (h) an illumination source positioned within the illumination channel, the illumination channel being adapted to receive the integrated illumination source positioned at the proximal channel opening of the illumination channel and guide the integrated illumination source positioned to the distal channel opening of the illumination channel as the integrated illumination source positioned is advanced into the illumination channel;
   at least one channel of the plurality of channels being configured to transfer fluid between the origin port and the destination port.

2. The guide sheath of claim 1, the first position sensor being configured to generate an electrical signal in response to a magnetic field, the electrical signal generated by the first position sensor being configured to indicate the position of the first position sensor within the magnetic field.

3. The guide sheath of claim 1, the origin port comprising a handle from which the shaft extends, the handle being adapted to be held in a hand during use.

4. The guide sheath of claim 1, further comprising a control wire with a first end fixed at the distal end of the guide sheath and a second end proximal to the first end, such that the second end may be retracted to cause the articulating portion to flex in a first direction.

5. The guide sheath of claim 4, a distance of displacement of the control wire within the guide sheath determining a degree to which the articulating portion flexes in the first direction.

6. The guide sheath of claim 4, the control wire being coupled at the first end to an articulation control, the articulation control being configured to retract the second end of the control wire and thereby cause the flex.

7. The guide sheath of claim 1, further comprising the IGS navigation system, the IGS navigation system being configured to display the current position of the destination port on a pre-operative image of a surgical site based on a signal from the first position sensor.

8. The guide sheath of claim 7, the IGS navigation system being further configured to determine a current flex of the articulating portion by comparing a current position of the first position sensor to a current position of the second position sensor and display the articulating portion on the pre-operative image based on the current position and the current flex.

9. The guide sheath of claim 8, the IGS navigation system being further configured to determine a position of a distal end of a deployed tool within a channel of the plurality of channels and display the position of the distal end of the deployed tool on the pre-operative image.

10. The guide sheath of claim 1, the first position sensor being configured to be integrated along an exterior surface of the destination port.

11. The guide sheath of claim 1, the first position sensor being configured to be integrated within an interior portion of the destination port.

12. The guide sheath of claim 1, the first position sensor comprising a circumferential sensor positioned around a circumference of the destination port.

13. The guide sheath of claim 1, the articulating portion of the shaft including a plurality of sections configured to articulate the articulating portion.

14. The guide sheath of claim 1, further comprising a third position sensor, the first and third position sensors being offset from one another around a circumference of the destination port.

15. The guide sheath of claim 1, the tool tracking sensor including a motion sensor.

16. The guide sheath of claim 1, the tool tracking sensor including a proximity sensor.

17. The guide sheath of claim 1, the tool tracking sensor including an optical sensor.

18. The guide sheath of claim 1, the tool tracking sensor being positioned at the origin port.

19. The guide sheath of claim 1, the tool tracking sensor being positioned at the destination port.

20. An image guided surgery (IGS) navigation system comprising:
(a) a magnetic field generator operable to provide a magnetic field;
(b) a guide sheath comprising:
(i) a shaft defining a central longitudinal axis and a plurality of channels, the shaft including a straight portion at a proximal end of the shaft, the shaft further including an origin port, the origin port being proximal to the straight portion, the plurality of channels including:
(A) at least one working channel configured to slidably receive an instrument, the at least one working channel being open at a distal end of the shaft,
(B) an endoscope channel configured to receive an endoscope, the endoscope channel being laterally offset from the central longitudinal axis and from the at least one working channel, and
(C) an illumination channel configured to transmit light or receive a light source, the illumination channel being laterally offset from the central longitudinal axis and from the at least one working channel,
(ii) an articulating portion at the end of the shaft, the articulating portion having a distal end and a destination port, the articulating portion being configured to articulate, the destination port being distal to the articulating portion, the straight portion being configured to remain straight during articulation of the articulating portion,
(iii) a first position sensor located at or distal to the distal end of the articulating portion, the articulating portion being operable to change the position of the distal end of the articulating portion relative to the shaft,
(iv) a second position sensor located proximal to the articulating portion and at the straight portion, the second position sensor being configured to operate with the magnetic field generator to determine a current position of the second position sensor, and
(v) an instrument tracking sensor, the instrument tracking sensor being configured to generate a signal indicating a distance to which an instrument is advanced in the working channel;
(c) a display;
(d) a flexible instrument positioned within a working channel of the least one working channel of the guide sheath, with a distal end of the flexible instrument being extendable from the distal end of the articulating portion, the flexible instrument comprising an irrigation and suction tool, the working channel being adapted to receive the irrigation and suction tool at a proximal opening of the working channel and guide the irrigation and suction tool to a distal opening of the working channel as the irrigation and suction tool is advanced into the tool channel; and
(e) a processor configured to:
(i) determine a current position of the first position sensor and a current position of the second position sensor within the magnetic field,
(ii) display a first representation of the position of a distal end of the guide sheath on a preoperative image in real-time based on a signal generated by the first position sensor in response to the magnetic field,
(iii) determine a current articulation of the articulating portion that is based on the respective current positions of the first position sensor and the second position sensor,
(iv) determine a position of the distal and proximal ends of the flexible instrument based, in part, on the determined current articulation of the articulating portion and on a signal from the instrument tracking sensor indicating a distance to which the flexible instrument is advanced in the working channel, and
(v) display a second representation of the position of the distal end of the flexible instrument on the preoperative image in real-time.

* * * * *